United States Patent [19]

Potthoff-Karl et al.

[11] Patent Number: 5,132,417

[45] Date of Patent: Jul. 21, 1992

[54] COPOLYMER BASED ON TERT-BUTYL ACRYLATE OR METHACRYLATE

[75] Inventors: Birgit Potthoff-Karl, Weinheim; Karin Sperling-Vietmeier, Neustadt; Axel Sanner, Frankenthal, all of Fed. Rep. of Germany

[73] Assignee: BASF Aktiengesellschaft, Ludwigshafen, Fed. Rep. of Germany

[21] Appl. No.: 438,306

[22] Filed: Nov. 20, 1989

[30] Foreign Application Priority Data

Dec. 15, 1988 [DE] Fed. Rep. of Germany ........ 3842183

[51] Int. Cl.$^5$ ................. C08F 26/08; C08L 37/00; A61K 7/09
[52] U.S. Cl. ..................... 526/264; 524/548; 424/71
[58] Field of Search .......... 526/264; 524/548; 424/71

[56] References Cited

FOREIGN PATENT DOCUMENTS 899078 9/1984 Belgium .
1911306 10/1970 Fed. Rep. of Germany .
2216260 2/1972 Fed. Rep. of Germany .
3627969 2/1988 Fed. Rep. of Germany .
3627970 2/1988 Fed. Rep. of Germany ...... 526/264

Primary Examiner—Joseph L. Schofer
Assistant Examiner—Alex H. Walker
Attorney, Agent, or Firm—Oblon, Spivak, McClelland, Maier & Neustadt

[57] ABSTRACT

Copolymers based on tert-butyl acrylate and/or tert-butyl methacrylate, having a K value of from 10 to 50 and obtainable by free radical polymerization of A) from 20 to 90% by weight of tert-butyl acrylate and/or tert-butyl methacrylate,
B) from 10 to 60% by weight of N-vinylpyrrolidone and
C) from 0 to 30% by weight of a $C_1$–$C_{20}$-alkyl acrylate, a $C_1$–$C_{20}$-alkyl methacrylate, a $C_2$–$C_4$-hydroxyalkyl acrylate, a $C_2$–$C_4$-hydroxyalkyl methacrylate or vinyl acetate or a mixture thereof, are used as film formers in hair setting compositions and compositions for the surface protection of two- or three-dimensional structures.

8 Claims, No Drawings

COPOLYMER BASED ON TERT-BUTYL ACRYLATE OR METHACRYLATE

The present invention relates to a copolymer based on tert-butyl acrylate or methacrylate, having a K value of from 10 to 50 and obtainable by free radical polymerization of A) from 20 to 90% by weight of tert-butyl acrylate or methacrylate,
B) from 10 to 60% by weight of N-vinylpyrrolidone and
C) from 0 to 30% by weight of a $C_1$–$C_{20}$-alkyl acrylate, a $C_1$–$C_{20}$-alkyl methacrylate, a $C_2$–$C_4$-hydroxyalkyl acrylate, a $C_2$–$C_4$-hydroxyalkyl methacrylate or vinyl acetate or a mixture thereof.

The present invention also relates to the use of this copolymer as a film former in hair setting compositions and compositions for the surface protection of two- or three-dimensional structures.

Hair setting compositions are increasingly based on spray formulations with hydrocarbons as blowing agents instead of halogenated hydrocarbons. The film formers used for this purpose are frequently polymers having acid or basic groups. For instance, DE-A-3,627,969 describes copolymers of N-vinylpyrrolidone, N-monoalkyl- or N,N-dialkyl-acrylamides and alkyl or hydroxyalkyl esters of acrylic or methacrylic acid and/or acrylic or methacrylic acid, and DE-A-3,627,970 describes terpolymers of N-vinylpyrrolidone, tert-butyl acrylate or methacrylate and acrylic or methacrylic acid.

For carboxyl-containing polymers to be properly compatible with, i.e. soluble in, the apolar hydrocarbons of the spray formulations, they must be neutralized with amines, for example with 2-amino-2-methylpropanol. This may result in odor problems during hair treatment. It is true that the hydrocarbon compatibility and equally the hair setting effect of these products are already at a high level, but improvements in these properties are still desirable.

Similar considerations as for hair sprays apply to sprays for protecting the surfaces of two- or three-dimensional structures. These protective films, which are also referred to as varnishes, are increasingly applied with the aid of sprays which contain hydrocarbons as blowing agents. For this application too, therefore, the hydrocarbon compatibility of the polymers needs to be improved.

BE-A-899,078 relates in general to copolymers composed of from 40 to 90 mol % of N-vinylpyrrolidone and from 10 to 60 mol % of one or more $C_2$–$C_8$-alkyl esters of acrylic or methacrylic acid. However, this reference describes only copolymers with an alkyl acrylate or methacrylate where the alkyl radical is unbranched. These copolymers are used as binders for medical dressings and similar products.

It is an object of the present invention to provide a film former for hair setting compositions and for the surface protection of two- or three-dimensional structures which shows good compatibility with apolar blowing agents based on hydrocarbons and also a persistently good hair setting or protective film effect.

We have found that this object is achieved by the copolymer defined at the beginning.

The copolymer according to the present invention is prepared from 20 to 90% by weight, preferably from 35 to 90% by weight, of tert-butyl acrylate or methacrylate as component A and from 10 to 60% by weight, preferably from 10 to 35% by weight, of N-vinylpyrrolidone as component B. Particularly good application properties are obtained with a composition of from 50 to 90% by weight of tert-butyl acrylate or methacrylate and from 10 to 30% by weight of N-vinylpyrrolidone.

In addition, the copolymer according to the present invention may incorporate up to 30% by weight, preferably up to 20% by weight, of a $C_1$–$C_{20}$-alkyl acrylate or methacrylate, for example methyl, ethyl, n-propyl, isopropyl, n-butyl, isobutyl, sec.-butyl, n-pentyl, n-hexyl, 2-ethylhexyl, n-octyl, n-nonyl, isononyl, n-decyl, n-dodecyl, n-tridecyl, isotridecyl, myristyl, cetyl, stearyl or eicosyl acrylate or methacrylate, of a $C_2$–$C_4$-hydroxyalkyl acrylate or methacrylate, for example 2-hydroxyethyl, 2-hydroxypropyl, 3-hydroxypropyl, 3-hydroxybutyl or 4-hydroxybutyl acrylate or methacrylate, of vinyl acetate or of a mixture thereof as component C. Component C may be in particular a $C_1$–$C_4$-alkyl acrylate or methacrylate, a hydroxypropyl acrylate or methacrylate or especially vinyl acetate.

The copolymer according to the present invention is prepared by free radical copolymerization of tert-butyl acrylate or methacrylate with N-vinylpyrrolidone and with or without one or more monomers C, preferably by solution polymerization in an organic solvent, in general an alcohol. This polymerization is customarily carried out at from 60° to 130° C. and at atmospheric pressure or under autogenous pressure.

Suitable initiators for the free radical polymerization reaction are the customary peroxo and azo compounds, for example dibenzoyl peroxide, tert-butyl perpivalate, tert-butyl per-2-ethylhexanoate, di-tert-butyl peroxide, tert-butyl hydroperoxide, 2,5-dimethyl-2,5-di(tert-butylperoxy)hexane or azobisisobutyronitrile, used advantageously in an amount of from 0.1 to 2% by weight, based on the weight of the monomers. The amounts of monomer and solvent are advantageously chosen in such a way as to obtain a 30–80% strength by weight solution of the copolymer.

The copolymer according to the present invention has a K value of from 10 to 50, preferably from 15 to 35. The particular desired K value can be set in a conventional manner via the polymerization conditions, primarily the polymerization time and the initiator concentration. The K value is measured by the method of Fikentscher, Cellulosechemie 13 (1932), 58–64, at 25° C. in 1.0% strength by weight solution in ethanol, and it is a measure of the molecular weight.

The copolymer according to the present invention customarily has a glass transition temperature of from 50° to 130° C., in particular from 60° to 100° C.

The copolymer according to the present invention is chiefly used as a film former in hair setting compositions, for example in hair gels and hair foams, and in particular as a styling aid in hair sprays. In addition, it may be used, preferably formulated as a spray, for the surface protection of two- or three-dimensional structures, for example drawings, maps, prints, photographs or pictures, through application of a transparent protective film.

Particularly preferred spray formulations for these two uses contain the following ingredients:

from 0.1 to 20% by weight, preferably from 0.5 to 10% by weight, in particular from 2 to 5% by weight, of the copolymer according to the present invention, from 10 to 95% by weight, preferably from 20 to 60% by weight, in particular from 30 to 50% by weight, of a customary solvent such as, in particular, ethanol or isopropanol or else acetone, n-propanol, n-butanol, 2-methoxy-1-propanol, n-pentane, n-hexane, cyclohexane, n-heptane, n-octane or dichloromethane or a mixture thereof, and from 5 to 90% by weight, preferably from 30 to 80% by weight, in particular from 45 to 70% by weight, of a customary blowing agent such as propane, n-butane, isobutane, 2,2-dimethylbutane, isopentane, dimethyl ether, fluorotrichloromethane, dichlorodifluoromethane or dichlorotetrafluoroethane or a mixture thereof. Of the compounds mentioned, in particular the hydrocarbons, and of these especially propane and n-butane, are used as blowing agents (gases). If desired, one or more of the chlorofluorocarbons mentioned may be included to form a blowing agent mixture, but only in a minor amount, up to about 20% by weight, based on the blowing agent mixture.

In addition, this spray formulation may contain a minor amount, for example 0.1 to 5.0% by weight, of a scent oil.

A standard spray formulation has for example the following composition:
3% by weight of the copolymer according to the present invention
30% by weight of ethanol
67% by weight of propane/n-butane in a weight ratio of 40:60.

A predominant part of the ethanol can be replaced by another solvent, for example a hydrocarbon such as n-pentane or n-hexane, without impairing the hair setting effect. The blowing agent used may also be n-butane alone.

The copolymer according to the present invention is highly compatible with apolar blowing agents in spray formulations, in particular with hydrocarbons such as propane or n-butane or mixtures thereof. In general, it gives a compatibility value of from 75 to 90% by weight, whereas the prior art polymers mentioned usually give values below 70% by weight. At the same time, the copolymer according to the present invention has a remarkably good hair setting effect, as evidenced by the high curl retention values, which are within the range from 80 to 95%.

EXAMPLE 1

Copolymer of tert-butyl acrylate and N-vinylpyrrolidone

A solution of 35 g of tert-butyl acrylate, 15 g of N-vinylpyrrolidone and 0.5 g of tert-butyl perpivalate in 275 g of ethanol was heated to 75° C. After the polymerization had started, as indicated by an increase in the viscosity, a mixture of 315 g of tert-butyl acrylate, 135 g of N-vinylpyrrolidone and 100 g of ethanol and a solution of 4.8 g of tert-butyl perpivalate in 120 g of ethanol were added simultaneously in the course of 6 hours during which the temperature was kept at 77°-80° C. by gentle boiling. Thereafter 3.0 g of 2,5-dimethyl-2,5-di(-tert-butylperoxy)hexane were added all at once, and the reaction vessel was sealed pressure-tight, heated to 130° C. and maintained at that temperature for 3 hours.

The polymer content of the solution obtained was 48.5% by weight. The copolymer had a K value of 19.3 (measured in a 1.0% strength by weight solution in ethanol at 25° C.) and a glass transition temperature of 75° C.

EXAMPLE 2

Copolymer of tert-butyl methacrylate and N-vinylpyrrolidone

The method of Example 1 was applied to tert-butyl methacrylate and N-vinylpyrrolidone to prepare an approximately 50% strength by weight copolymer solution in ethanol. The copolymer had a K value of 21.1 (measured on a 1.0% strength by weight solution in ethanol at 25° C.) and a glass transition temperature of 87° C.

EXAMPLE 3

Copolymer of tert-butyl acrylate, N-vinylpyrrolidone and vinyl acetate

A mixture of 60 g of tert-butyl acrylate, 30 g of N-vinylpyrrolidone, 10 g of vinyl acetate, 0.7 g of tert-butyl perpivalate and 60 g of ethanol was heated to 75° C. After the polymerization had started, as indicated by an increase in viscosity, a mixture of 540 g of tert-butyl acrylate, 270 g of N-vinylpyrrolidone, 90 g of vinyl acetate and 550 g of ethanol and a solution of 6.0 g of tert-butyl perpivalate in 90 g of ethanol were added simultaneously in the course of 6 hours during which the temperature was maintained at 77°-80° C. by gentle boiling. Thereafter a solution of 3.0 g of 2,5-dimethyl-2,5-di(tert-butylperoxy)hexane in 400 g of ethanol was added, and the reaction kettle was sealed pressure-tight, heated to 130° C. and maintained at that temperature for 3 hours.

The polymer content of the solution obtained was 47.7% by weight. The terpolymer had a K value of 22.9 (measured on a 1.0% strength by weight solution in ethanol at 25° C.) and a glass transition temperature of 79° C.

EXAMPLES 4 TO 12

Examples 4 to 12 (see table) concern copolymers of tert-butyl acrylate and N-vinylpyrrolidone or tert-butyl acrylate, N-vinylpyrrolidone and vinyl acetate, each in a different composition. Products 4 to 9 were prepared as described in Example 1 and products 10 to 12 as described in Example 3.

Properties of the Copolymers

The table below shows the composition, the hydrocarbon compatibility and hair setting effect of each of the copolymers of Examples 1 to 12. For comparison, the corresponding properties have been indicated for two copolymers as described in DE-A-3,627,970 under Examples A and B.

TABLE

Composition, hydrocarbon compatibility and curl retention of hair spray formulations

| Example | Composition [% by weight] | | | | | Hydrocarbon compatibility with propane/n-butane (40:60) [% by weight] | Curl retention [%] |
| --- | --- | --- | --- | --- | --- | --- | --- |
| | tBA | tBMA | VP | VAc | AA | | |

TABLE-continued

Composition, hydrocarbon compatibility and curl retention of hair spray formulations

| | Composition [% by weight] | | | | | Hydrocarbon compatibility with propane/n-butane (40:60) [% by weight] | Curl retention [%] |
|---|---|---|---|---|---|---|---|
| | tBA | tBMA | VP | VAc | AA | | |
| 1 | 70 | | 30 | | | 83 | 93 |
| 2 | | 70 | 30 | | | 81 | 89 |
| 3 | 60 | | 30 | 10 | | 80 | 85 |
| 4 | 40 | | 60 | | | 76 | 78 |
| 5 | 50 | | 50 | | | 77 | 93 |
| 6 | 60 | | 40 | | | 81 | 90 |
| 7 | 75 | | 25 | | | 84 | 90 |
| 8 | 85 | | 15 | | | 88 | 83 |
| 9 | 90 | | 10 | | | 89 | 89 |
| 10 | 45 | | 40 | 15 | | 72 | 86 |
| 11 | 70 | | 25 | 5 | | 82 | 86 |
| 12 | 80 | | 15 | 5 | | 83 | 89 |
| Comparative examples* | | | | | | | |
| A | 50 | | 40 | | 10 | 71 | 56 |
| B | | 50 | 40 | | 10 | 64 | 75 | tBA: tert-butyl acrylate,
tBMA: tert-butyl methacrylate,
VP: vinylpyrrolidone,
*as per Examples 2 and 3 of DE-A-3,627,970

The hydrocarbon compatibility with a propane/n-butane mixture in a weight ratio of 40:60 indicates the maximum percentage by weight of this blowing gas mixture which a spray formulation which, besides ethanol as solvent, contains 3% by weight of the copolymer may contain without cloudiness occurring at 0° C.

The curl retention is a measure of the hair setting effect. It is measured on hair curls produced by conventional perming from hair approximately 15 cm in length and sprayed with the particular spray formulation from a distance of 10 cm for 4 seconds. After the suspended curls have been conditioned at 25° C. and 90% relative humidity for 5 hours, the relative uncurling of the curls from their original shape is determined. A high value indicates a high degree of curl retention; that is, 100% indicates that the original curl shape is completely intact.

The curl retention was determined in each case with the following standard spray formulation:
3% by weight of the copolymer according to the present invention
30% by weight of ethanol
67% by weight of propane/n-butane (40:60)

EXAMPLE 13

Spray Formulation for the Surface Protection of Two-Dimensional Structures

A spray formulation formed from
3% by weight of copolymer of Example 8 (85% by weight of tert-butyl acrylate, 15% by weight of N-vinylpyrrolidone)
20% by weight of ethanol
30% by weight of N-hexane
47% by weight of n-butane
was used to spray a printed paper. A transparent, durable and soil repellant protective film was obtained.

We claim:

1. A copolymer based on tert-butyl acrylate, tert-butyl methacrylate or a mixture thereof and having a K value of from 10 to 50, obtained by free radical polymerization of a composition consisting of:

A) from 20 to 90% by weight of tert-butyl acrylate, tert-butyl methacrylate or a mixture thereof
B) from 10 to 60% by weight of N-vinylpyrrolidone and
C) from 0 to 30% by weight of a $C_1$-$C_{20}$-alkyl acrylate, a $C_1$-$C_{20}$-alkyl methacrylate, a $C_2$-$C_4$-hydroxyalkyl acrylate, a $C_2$-$C_4$-hydroxylakyl methacrylate or vinyl acetate or a mixture thereof.

2. A copolymer as claimed in claim 1, obtained by free radical polymerization of a composition consisting of:

A) from 35 to 90% by weight of tert-butyl acrylate, tert-butyl methacrylate or a mixture thereof,
B) from 10 to 35% by weight of N-vinylpyrrolidone and
C) from 0 to 30% by weight of component C.

3. A process for preparing a copolymer as claimed in claim 1 comprising free radical polymerization of a composition consisting of:

A) from 20 to 90% by weight of tert-butyl acrylate, tert-butyl methacrylate or a mixture thereof
B) from 10 to 60% by weight of N-vinylpyrrolidone and
C) from 0 to 30% by weight of component C.

4. A process for preparing a copolymer as claimed in claim 2 comprising free radical polymerization of a composition consisting of:

A) from 35 to 90% by weight of tert-butyl acrylate, tert-butyl methacrylate or a mixture thereof,
B) from 10 to 35% by weight of N-vinylpyrrolidone and
C) from 0 to 30% by weight of component C.

5. A hair setting composition containing a copolymer as claimed in claim 1 as film former.

6. A composition for the surface protection of two- or three-dimensional structures containing a copolymer as claimed in claim 1 as film former.

7. A hair spray formulation containing besides customary solvents and blowing agents from 0.1 to 20% by weight of a copolymer as claimed in claim 1.

8. A spray formulation for the surface protection of two- or three-dimensional structures containing besides customary solvents and blowing agents from 0.1 to 20% by weight of copolymer as claimed in claim 1.

* * * * *